US011701222B2

(12) United States Patent
Muchhala et al.

(10) Patent No.: US 11,701,222 B2
(45) Date of Patent: Jul. 18, 2023

(54) INJECTOR ASSEMBLY EMPLOYING COMPRESSED GAS AND A MECHANICAL BRAKE FOR PRESENTING AN INTRAOCULAR LENS TO A PATIENT

(71) Applicant: Bausch & Lomb Incorporated, Rochester, NY (US)

(72) Inventors: Sushant P. Muchhala, Aliso Viejo, CA (US); Moises A. Valle, Tustin, CA (US); Madhu S. Ayyagari, Rancho Santa Margarita, CA (US); Sanjeev Bakshi, Trabuco Canyon, CA (US); Jeffrey C. Smith, Lake Forest, CA (US); Andrew J. Scherer, Jr., Trabuco Canyon, CA (US); Mark E. Mossberg, Santa Ana, CA (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 16/364,968

(22) Filed: Mar. 26, 2019

(65) Prior Publication Data

US 2019/0298512 A1 Oct. 3, 2019

Related U.S. Application Data

(60) Provisional application No. 62/649,353, filed on Mar. 28, 2018.

(51) Int. Cl.
*A61F 2/16* (2006.01)
*A61B 90/00* (2016.01)
(Continued)

(52) U.S. Cl.
CPC ............ *A61F 2/167* (2013.01); *A61F 2/1662* (2013.01); *A61F 2/1672* (2013.01);
(Continued)

(58) Field of Classification Search
CPC .... A61F 2/1662; A61F 2/1664; A61F 2/1667; A61F 2/167; A61F 2/1672; A61F 2/1675; A61F 2/1678
See application file for complete search history.

(56) References Cited

U.S. PATENT DOCUMENTS 6,010,510 A * 1/2000 Brown .................... A61F 2/167
606/107
6,503,275 B1 1/2003 Cumming
(Continued)

FOREIGN PATENT DOCUMENTS

EP 0363213 A2 10/1989
EP 1491163 A2 12/2004
(Continued)

OTHER PUBLICATIONS

European Patent Office, International Search Report and Written Opinion in PCT/US19/24053 completed Jul. 10, 2019 and dated Jul. 17, 2019.

*Primary Examiner* — Darwin P Erezo
*Assistant Examiner* — Christian D. Knauss
(74) *Attorney, Agent, or Firm* — Brian B. Shaw, Esq.; Harter Secrest & Emery LLP (57) ABSTRACT

An intraocular lens (IOL) injector is configured for single hand operation and employs a compressed gas to provide a motive force to present an IOL to a surgical site. The IOL injector includes a mechanical brake coupled to a plunger to preclude translation of an IOL absent operator input. The mechanical brake provides for selectively varying the speed and translation of the plunger, and hence IOL during presentation of the IOL to a patient. The IOL injector can also include at least a first stop, which halts movement of the plunger at a predetermined position. The at least first stop is then moved to a passing position, thereby allowing further (Continued)

operator controlled translation of the plunger to present the IOL to the surgical site.

12 Claims, 7 Drawing Sheets

(51) Int. Cl.
*A61B 17/00* (2006.01)
*A61F 2/14* (2006.01)

(52) U.S. Cl.
CPC ............. *A61B 2017/00367* (2013.01); *A61B 2017/00398* (2013.01); *A61B 2090/034* (2016.02); *A61F 2/148* (2013.01); *A61F 2/1664* (2013.01); *A61F 2/1678* (2013.01)

(56) References Cited

U.S. PATENT DOCUMENTS

| | | | |
|---|---|---|---|
| 8,246,631 | B2 | 8/2012 | Pynson |
| 8,535,332 | B2 | 9/2013 | Pynson |
| 8,579,969 | B2 | 11/2013 | Zacharias |
| 8,758,433 | B2 | 6/2014 | Cole et al. |
| 8,801,780 | B2 | 8/2014 | Chen |
| 8,920,494 | B2 | 12/2014 | Catlin et al. |
| 8,998,983 | B2 | 4/2015 | Auld |
| 9,155,615 | B2 | 10/2015 | Valle et al. |
| 9,421,129 | B2 | 8/2016 | Lerner |
| 2004/0111094 | A1* | 6/2004 | Meyer ............... A61F 2/1664 606/107 |
| 2005/0283162 | A1 | 12/2005 | Stratas |
| 2008/0004610 | A1 | 1/2008 | Miller et al. |
| 2009/0018548 | A1 | 1/2009 | Charles |
| 2010/0160926 | A1 | 6/2010 | Artsyukhovich |
| 2011/0264101 | A1 | 10/2011 | Inoue et al. |
| 2014/0200590 | A1 | 7/2014 | Chen |
| 2014/0257317 | A1 | 9/2014 | Safabash |
| 2014/0276901 | A1 | 9/2014 | Auld |
| 2015/0028928 | A1 | 1/2015 | King |
| 2015/0088149 | A1 | 3/2015 | Auld |
| 2015/0342726 | A1* | 12/2015 | Deacon ............... A61F 2/1662 623/6.12 |
| 2016/0000556 | A1 | 1/2016 | Perera |
| 2016/0015511 | A1 | 1/2016 | Auld et al. |
| 2016/0067036 | A1 | 3/2016 | Auld |
| 2017/0207641 | A1* | 7/2017 | Schmidt ............... H02J 9/002 |
| 2017/0367816 | A1* | 12/2017 | Fayyaz ............... A61F 2/1672 |

FOREIGN PATENT DOCUMENTS

| | | |
|---|---|---|
| EP | 1845898 B1 | 8/2011 |
| EP | 2675393 B1 | 1/2016 |
| EP | 2560578 B1 | 6/2016 |
| EP | 2854708 B1 | 10/2016 |
| EP | 2355747 B1 | 11/2016 |
| JP | 469452 B2 | 7/2012 |
| JP | 5723039 B2 | 5/2015 |
| JP | 5723040 B2 | 5/2015 |
| JP | 2015517893 A | 6/2015 |
| WO | 1998020819 A1 | 5/1998 |
| WO | 2006059183 A1 | 6/2006 |
| WO | 2009012017 A1 | 1/2009 |
| WO | 2010044974 A1 | 4/2010 |
| WO | 2011133853 A1 | 10/2011 |
| WO | 2012018547 A1 | 2/2012 |
| WO | 2012129419 A1 | 9/2012 |
| WO | 2013184727 A1 | 12/2013 |
| WO | 2014089250 A1 | 6/2014 |
| WO | 2014129977 A1 | 8/2014 |
| WO | 2014137983 A1 | 9/2014 |
| WO | 2015154049 A1 | 10/2015 |
| WO | 2016011215 A1 | 1/2016 |

\* cited by examiner

INJECTOR ASSEMBLY EMPLOYING COMPRESSED GAS AND A MECHANICAL BRAKE FOR PRESENTING AN INTRAOCULAR LENS TO A PATIENT

STATEMENT REGARDING FEDERALLY SPONSORED RESEARCH OR DEVELOPMENT

Not applicable.

REFERENCE TO A "SEQUENCE LISTING"

Not applicable.

BACKGROUND OF THE INVENTION

Field of the Invention

The present disclosure relates to an intraocular lens (IOL) injector and particularly to an IOL injector using compressed gas as a motive force for presenting an IOL to a patient, and more particularly to a disposable IOL injector using compressed gas as the motive force.

Description of Related Art

Intraocular lenses (also referred to herein as IOLs or simply as lenses) are artificial lenses used to replace natural crystalline lenses of eyes when the natural lenses are diseased or otherwise impaired. Under some circumstances a natural lens may remain in an eye together with an implanted IOL. IOLs may be placed in either the posterior chamber or the anterior chamber of an eye.

IOLs come in a variety of structures and materials. Various instruments and methods for implanting such IOLs in an eye are known. Typically, an incision is made in a cornea and an IOL is inserted into the eye through the incision. In one technique, a surgeon uses surgical forceps to grasp the IOL and insert it through the incision into the eye. While this technique is still practiced today, more and more surgeons are using IOL injectors which can offer advantages such as affording a surgeon more control when inserting an IOL into an eye and permitting insertion of IOLs through smaller incisions. Smaller incision sizes (e.g., less than about 3 mm) are preferred over larger incisions (e.g., about 3.2 to 5+ mm) since smaller incisions have been associated with reduced post-surgical healing time and reduced complications such as induced astigmatism.

In order for an IOL to fit through a smaller incision, the IOL is typically folded and/or compressed prior to entering an eye where it will assume its original unfolded/uncompressed shape. Since IOLs are very small and delicate articles of manufacture, they are susceptible to damage in handling and presentation to the eye.

It is desirable that an IOL be expelled from the tip of the IOL injector and into the eye in an undamaged condition in a predictable orientation, with a predictable speed and force.

Various IOL injectors and other devices have been proposed which attempt to address issues related to presenting the IOL to the patient, yet the desired control of the IOL injector requires the operator to use two hands and the single hand designs of the IOL injector do not provide the desired control of the injection of the IOL. Thus, there remains a need for an injector assembly which provides controllable insertion performance and allows the injector assembly to be manipulated with a single hand.

BRIEF SUMMARY OF THE INVENTION

The present disclosure provides an IOL injector for single hand control, manipulation and operation, and in select configurations the IOL injector is single use or disposable. That is, the present construction and application of compressed gas as the motive force provides sufficient cost savings to render the IOL injector disposable.

The present disclosure also provides an intraocular lens, (IOL) injector having a compressed gas reservoir for retaining a compressed gas; a guide shaft assembly exposed to the compressed gas reservoir, the guide shaft assembly being moveable along a longitudinal direction from a retracted position to an extended position; and a mechanical brake operably coupled to the guide shaft assembly, the mechanical brake being configured to exert on the guide shaft assembly, in response to an operator actuation, a variable resistance to the longitudinal movement of the guide shaft, the mechanical brake having a default engagement with the guide shaft assembly sufficient to preclude movement of the guide shaft assembly in response to exposure of the guide shaft assembly to compressed gas in the compressed gas reservoir.

The present disclosure further provides for an IOL injector having an IOL support configured to receive and retain an IOL for presentation to an eye of a patient; a compressed gas reservoir; a guide shaft assembly exposed to the compressed gas reservoir to translate from a retracted position spaced from the IOL to an extended position contacting and displacing the IOL from the IOL support for insertion into an eye of a patient; a mechanical brake having a default position applying sufficient mechanical resistance to the guide shaft assembly to preclude movement of the guide shaft assembly upon exposure of the guide shaft assembly to the compressed gas in the compressed gas reservoir; and a moveable control surface connected to the brake to move the mechanical brake from the default position to apply a variable mechanical resistance to movement of the guide shaft assembly from the retracted position to the extended position in response to exposure to the compressed gas in the compressed gas reservoir.

The present disclosure further contemplates a method including disposing a guide shaft assembly within an injector body to be moveable along a longitudinal direction from a retracted position to an extended position, wherein the guide shaft assembly is exposed to a compressed gas reservoir for retaining a compressed gas; and engaging a mechanical brake with the guide shaft assembly, the mechanical brake configured to exert on the guide shaft assembly in response to an operator actuation a variable resistance to the longitudinal movement of the guide shaft, the mechanical brake having a default engagement with the guide shaft assembly to preclude movement of the guide shaft assembly in response to exposure of the guide shaft to compressed gas in the compressed gas reservoir.

Also disclosed is an IOL injector having an injector body; a guide shaft assembly having a plunger, the guide shaft assembly moveable relative to the injector body between a retracted position and an extended position in response to a motive force; a mechanical brake connected to the plunger for controlling movement of the plunger in response to the motive force; and a first stop moveably connected to the injector body between a blocking position and a passing position, the first stop in the blocking position precluding movement of the guide shaft assembly toward the extended position and the first stop in the passing position permitting movement of the guide shaft assembly toward the extended position. As the first stop is located to permit movement of the guide shaft assembly from the retracted position toward the extended position and preclude movement of the guide shaft assembly to the extended position, a surgical technician can prepare the IOL injector for use by the surgeon by moving the guide shaft assembly from the retracted position to the position of the first stop (to at least contact a portion of the guide shaft assembly with the IOL in the IOL injector) while reducing the risk of spontaneous ejection of the IOL from the IOL injector. It is also contemplated the guide shaft assembly can be a plunger. The IOL injector can further include a second stop moveably connected to the injector body between a blocking position and a passing position the second stop in the blocking position precluding movement of the guide shaft assembly toward the extended position and the second stop in the passing position permitting movement of the guide shaft assembly toward the extended position.

The disclosure also provides a method including the steps of exposing a guide shaft assembly to a compressed gas to move a plunger from a retracted position toward an extended position to contact a first stop, the first stop being in a blocking position precluding further movement of the guide shaft assembly towards the extended position; moving the first stop from the blocking position to a passing position; and controlling a mechanical brake to permit movement of the guide shaft assembly from the position of the first stop toward the extended position. The method further provides that the guide shaft assembly may include a plunger movement of the guide shaft assembly and plunger from the retracted position to the first stop at least partly folds the IOL within the IOL injector. Thus, a surgical technician can prepare the IOL injector for a surgeon by moving the plunger to contact the IOL and at least partially transition the IOL to an injection configuration within the IOL injector and then contact one of the guide shaft assembly and the plunger with the first stop, thereby reducing a risk of spontaneous ejection of the IOL from the IOL injector.

Another method is disclosed including the steps of translating a guide shaft assembly from a retracted position toward an extended position to contact a first stop, the first stop being in a blocking position precluding further movement of the guide shaft assembly towards the extended position; moving the first stop from the blocking position to a passing position; and controlling a mechanical brake to permit movement of the guide shaft assembly from the position of the first stop toward the extended position. The method can also provide that movement of the guide shaft assembly from the retracted position to the first stop at least partly folds an IOL within the IOL injector. A further step in the method includes translating the guide shaft assembly from the first stop towards the extended position to contact a second stop, the second stop being in a blocking position precluding further movement of the guide shaft assembly towards the extended position. Another step in the method can include moving the second stop from the blocking position to a passing position and moving the guide shaft assembly a sufficient distance to vent compressed gas from the IOL injector.

DETAILED DESCRIPTION OF THE INVENTION

Generally, the present disclosure provides an IOL injector 10 for presenting an IOL 20 to a surgical site, wherein the IOL injector can be operably controlled with one hand. In certain configurations, the IOL injector 10 is configured to be single use or disposable.

Referring to FIGS. 1-4 and 10, the IOL injector 10 includes an injector body 30, a guide shaft assembly 50 having a guide shaft 52, a piston 60 and a plunger 80, a compressed gas reservoir 32 and a mechanical brake 110 which cooperate for selectively presenting an IOL 20 to a patient.

Figure 14:
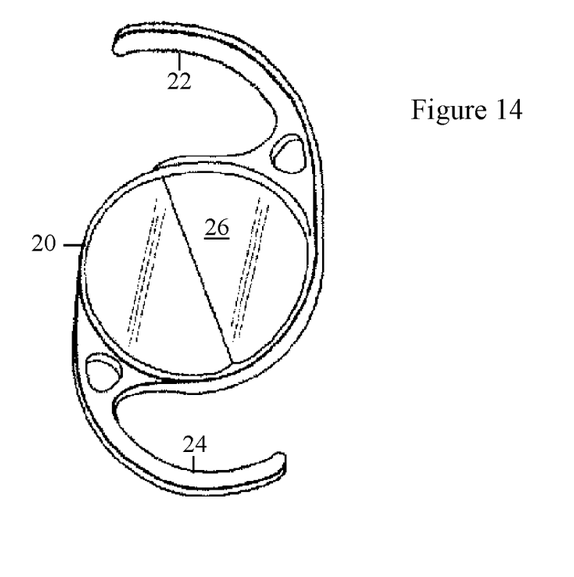
FIG. 14 is a representative intraocular lens.

As used herein, the IOL 20 is an artificial lens used to replace the natural crystalline lens of the eye when the natural lens has cataracts or is otherwise diseased. IOLs 20 are also sometimes implanted into an eye to correct refractive errors of the eye in which case the natural lens may remain in the eye together with the implanted IOL. The IOL 20 may be placed in either the posterior chamber or anterior chamber of the eye. IOLs 20 come in a variety of structures and materials. Referring to FIG. 14, some common IOL 20 styles include the so-called open-looped haptics which include the three-piece type having an optic and two haptics 22, 24 attached to and extending from an optic 26; the one-piece type wherein the optic and haptics are integrally formed (e.g., by machining the optic and haptics together from a single block of material); and also the closed looped haptic IOLs. A further style of IOL is called the plate haptic type wherein the haptics are configured as a flat plate extending from opposite sides of the optic. The IOL 20 may be made from a variety of materials or combination of materials such as, but not limited to PMMA, silicone, hydrogels and silicone hydrogels.

It is also understood that the IOL 20 structure shown and described herein is for discussion purposes only, and that the present disclosure is not to be limited by the particular structure of the IOL. The present system may be easily adapted to IOLs 20 of any structure and type (e.g., IOLs with plate, open or closed loop haptics, anterior chamber IOLs, posterior chamber IOLs, accommodating IOLs (including single and double lens types), etc.). The IOL 20 has a nominal state in the absence of external forces (other than gravity). That is, the nominal state is the formation the IOL assumes upon the removal of deforming forces.

Injector Body

The injector body 30 is a generally elongate member sized to retain the guide shaft assembly 50, the mechanical brake 110 and at least a portion of the compressed gas reservoir 32, wherein compressed gas is used as the motive force for selectively presenting the IOL 20 to the patient. The injector body 30 defines a longitudinal axis (LA) extending along a major length of the injector body wherein movement along the longitudinal axis is movement in a longitudinal direction.

The injector body 30 can include a left side housing 31 and a right side housing 33, which define a lumen 39 extending along the longitudinal axis. The lumen 39 can have any of a variety of cross-sectional profiles, wherein circular or oval shapes are typical. Further, the lumen 39 can include a plurality of sections, wherein the sections are parallel but non-collinear. The sections of the lumen can be configured to slideably receive corresponding portions of the guide shaft assembly 50, as set forth below. Thus, certain sections of the lumen 39 can receive different portions of the longitudinally displaceable components of the IOL injector 10, thereby reducing an overall longitudinal dimension of the injector body 30. A portion of the injector body 30 may include a configured surface for engaging a portion of a hand of the operator. It is understood that the overall structure of the injector body 30 may vary from that shown and described herein. It is furthermore understood that the components of the injector body 30 may be made of any suitable material (e.g., polypropylene) and may be wholly or partly opaque, transparent or translucent to better visualize (i) the IOL 20 within the IOL injector 10 and (ii) the IOL delivery sequence. The material of the injector body 30 can be selected to provide for the structure being disposable or recyclable, such as in a single use configuration.

In one configuration, the injector body 30 includes a port or interface for receiving and an IOL support for retaining an IOL 20. The interface and IOL support can be configured to accept and retain a single free IOL 20 or can be configured to accept and retain a carry or cartridge such as a shuttle 130, wherein the shuttle as the IOL support retains the IOL 20 for being presented to the patient. Specifically in one configuration, referring to FIGS. 1-4, the injector body 30 includes the interface and a shuttle bay 45 opening into the lumen 39. The shuttle bay 45 receives or accepts the shuttle 130 for operable engagement with the injector body 30. The shuttle bay 45 includes engaging surfaces for engaging the shuttle 130. The engaging surfaces can include alignment surfaces for contacting the shuttle 130 in predetermined locations to provide accurate and reproducible retention of the shuttle in the injector body 30. The shuttle 130 thus functions as the IOL support and can be any of a variety of configurations and is not a limiting feature of the present system. Typically, the shuttle 130 includes a shuttle lumen aligned with at least a portion of the lumen 39 of the injector 10.

In one embodiment, the injector body 30 further cooperates with an injector tip 54 which defines an extension of the lumen 39 so as to define a pathway of the IOL 20 to the eye of the patient. The injector tip 54 defines a terminal end having a size for insertion into or presentation to the eye, with the IOL 20 correspondingly deformed within the injector tip. However, it is understood, the shuttle 130 can include an integral injector tip or nozzle defining a portion of the lumen 39 for directing the IOL 20 to the patient.

The injector body 30 can include the compressed gas reservoir 32 for retaining, generating or receiving compressed gas, such as from a compressed gas cartridge 124. As set forth below, the compressed gas reservoir 32 is partly defined by (exposed to) the piston 60. Depending on the intended operating parameters of the IOL injector 10, the compressed gas cartridge 124 can be coupled with the injector body 30 to preclude non-destructive separation, thus providing a feature supporting the single use characteristics of the IOL injector.

The injector body 30 can define at least a portion of the compressed gas reservoir 32, wherein the compressed gas cartridge 124 can further define a portion of the compressed gas reservoir. It is understood a separate component can be engaged or coupled to the injector body 30 to define a portion of the compressed gas reservoir 32. The compressed gas reservoir 32 receives compressed gas from the compressed gas cartridge 124 or other source of compressed gas. Thus, it is understood the compressed gas reservoir 32 can be a separate cartridge, an internal volume of the injector body 30 or a cartridge in conjunction with an internal volume of the injector body 30 that retains a sufficient volume or mass of compressed gas.

The compressed gas can be any of a variety of gases or mixtures that are biologically compatible with the IOL 20 and the patient. The compressed gas can be provided by the cartridge 124, a pump, a fan, a compressor or any other mechanism for generating a volume of the compressed gas. In one configuration, the compressed gas is initially retained in the compressed gas cartridge 124. In the configuration employing the compressed gas cartridge 124, it is contemplated the cartridge is carried by the IOL injector 10 and is selectively pierced to release the compressed gas.

In one configuration, the injector body 30 includes a cap 34 for retaining the compressed gas cartridge 124 and a piercing pin 36 aligned with a seal of the compressed gas cartridge or canister 124. The seal of the compressed gas cartridge 124 can be selectively pierced by movement of the cap 34, the piercing pin 36 or a combination of both, wherein the released gas fills the compressed gas reservoir 32 of the injector body 30 and thus acts on the guide shaft assembly 50 via the piston 60.

Figure 7:
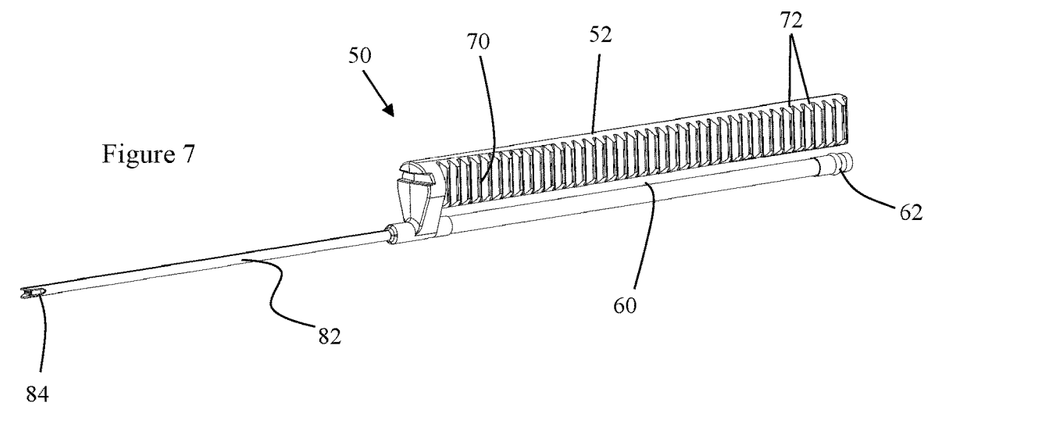
FIG. 7 is a perspective view of a left side of the guide shaft assembly having a guide shaft, a plunger and a piston.
Figure 8:
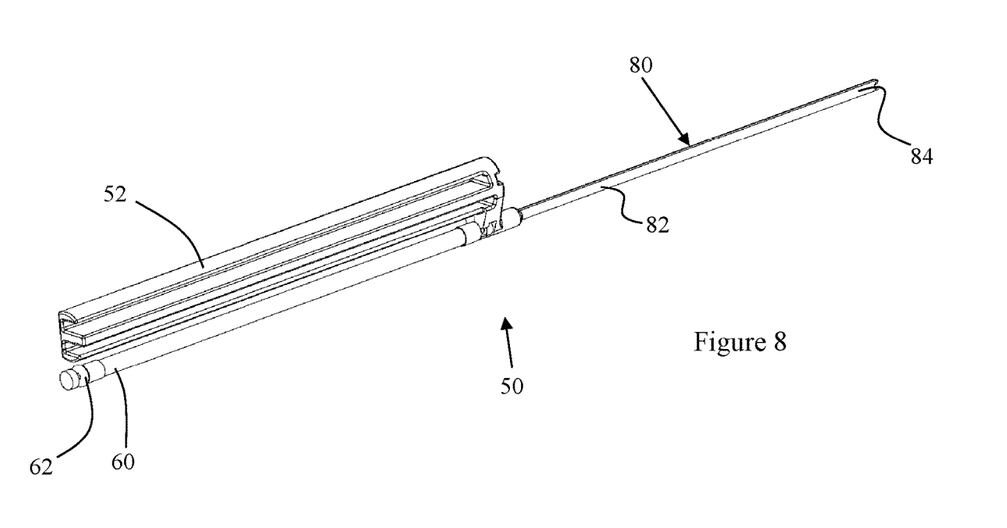
FIG. 8 is a perspective view of a right side of the guide shaft assembly of FIG. 7 having a guide shaft, a plunger and a piston.
Figure 9:
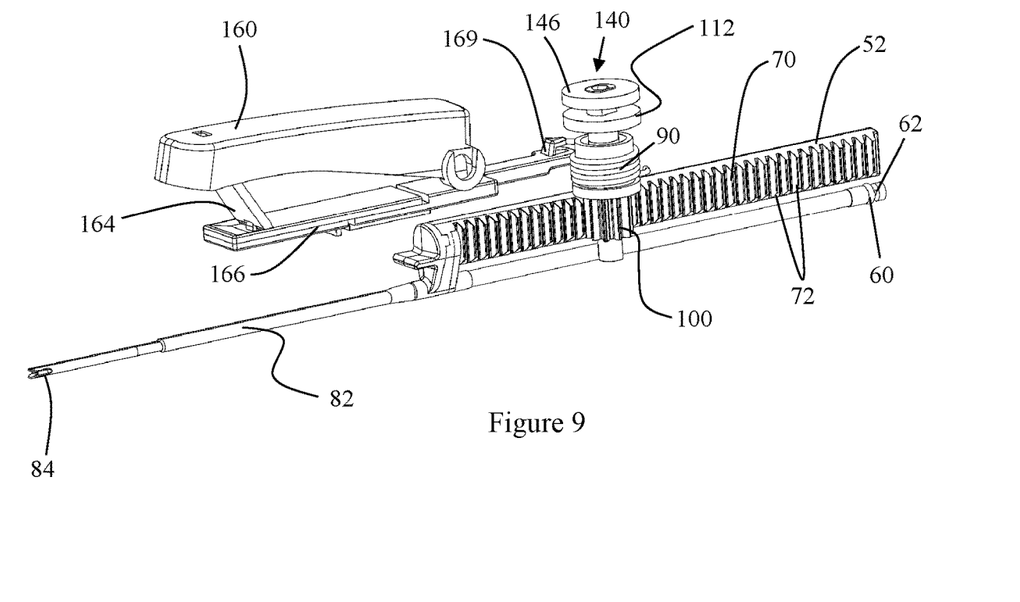
FIG. 9 is a perspective view of a left side of the guide shaft assembly and a mechanical brake of the IOL injector.
Figure 10:
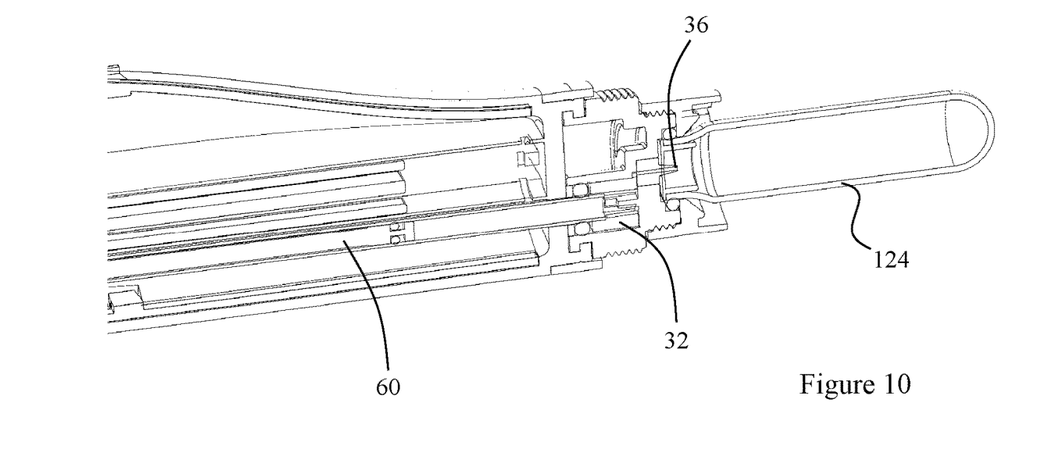
FIG. 10 is a perspective cross sectional view of the compressed gas cartridge in the IOL injector.
Figure 11:
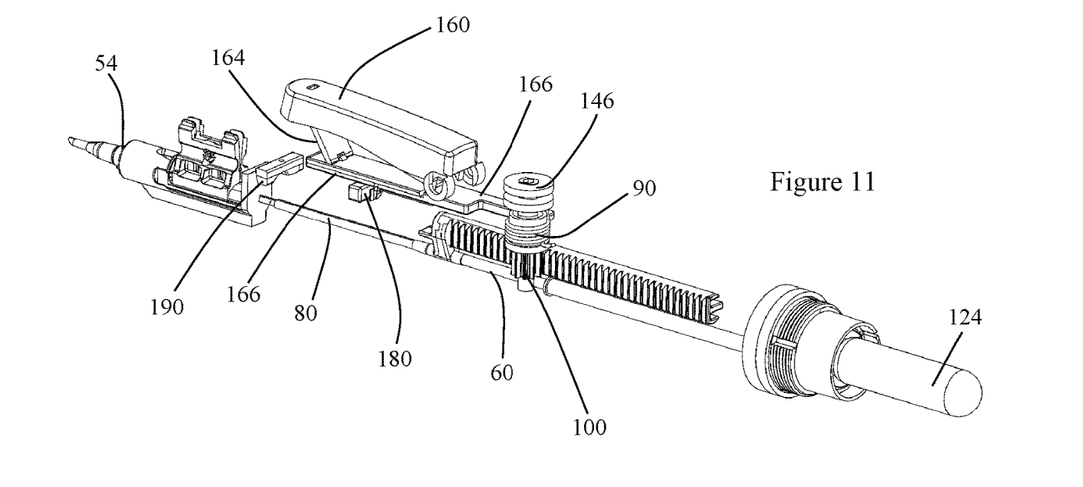
FIG. 11 is a left side perspective view of the IOL injector of FIG. 1 with the housing components being removed for clarity.
Figure 12:
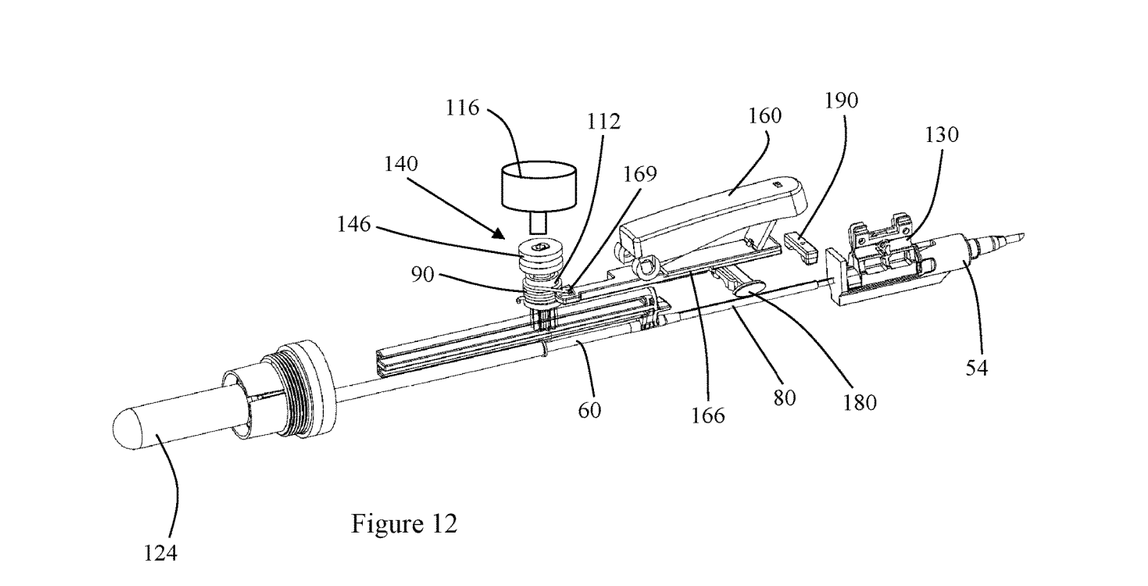
FIG. 12 is a right side perspective view of the IOL injector of FIG. 1 with housing components being removed for clarity.

In one configuration, the guide shaft assembly 50 having the guide shaft 52, the piston 60 and the plunger 80 are longitudinally overlapping to reduce an overall dimension along the longitudinal axis. That is, rather than coaxially aligning the guide shaft 52, the piston 60 and the plunger 80 end to end along the longitudinal dimension, a portion of the length of the piston is coextensive with a portion of the guide shaft, thereby reducing the overall length of the guide shaft assembly 50. For example, as seen in FIGS. 7, 8, and 9, a majority of a length of the guide shaft 52 and a majority of a length of the piston 60 occupy a common length along the longitudinal direction, referring to FIG. 4. The guide shaft 52, the piston 60 and the plunger 80 are connected such that movement or any one of the components results in a corresponding movement of the remaining components along the longitudinal direction along the longitudinal axis.

The guide shaft 52 of the guide shaft assembly 50 can include or be coupled to the piston 60 and the plunger 80. The guide shaft 52, the piston 60 and the plunger 80 can thus be integral or individually formed components that are subsequently joined. Further, the guide shaft assembly 50 can be of various configurations to provide the functionality of the piston 60 and the plunger 80. For purposes of description, all such configurations are referred to as the guide shaft assembly 50. Thus, as the piston 60 moves along the longitudinal direction, both the guide shaft 52 and the plunger 80 correspondingly move along the longitudinal direction.

The piston 60, and hence guide shaft assembly 50, is slideably connected to the injector body 30 and defines a portion of the compressed gas reservoir 32. As set forth below, the piston 60 is connected to the guide shaft 52 and thus coupled in turn to the mechanical brake 110. The piston 60 is movable between a fixed, retracted or braked, first position and an actuated or extended second position. The piston 60 includes a seal 62 for forming a sealed interface with the injector body 30. One section of the lumen 39 of the injector body 30 includes an inner surface 42 forming a sealed interface with the piston 60 as the piston moves in response to exposure to the compressed gas.

Referring to FIGS. 7 and 8, the plunger 80 includes a plunger shaft 82 and a plunger tip 84 configured for engaging the IOL 20 and specifically the optic 26 at the periphery of the optic as the plunger is advanced along the shuttle lumen. It is understood that other plunger tip designs may be used with the present system. It is furthermore preferred that the plunger shaft 82 is rotationally fixed within the lumen 39 to prevent unexpected rotation of the plunger shaft (and thus the plunger tip 84) relative to the lumen. The plunger shaft 82 may be rotationally fixed by forming the proximal shaft length and lumen non-circular in cross-section or by including rotational fixing elements on the lumen inner wall and plunger shaft (e.g., longitudinal flange on the plunger having a sliding fit within a longitudinally extending groove provided on the lumen inner wall).

The plunger shaft 82 is connected to or driven by the guide shaft 52 such that movement of the guide shaft along the longitudinal axis correspondingly moves the plunger 80 along the longitudinal axis. Thus, in one configuration, the piston 60, the guide shaft 52 and the plunger 80 move as a single unit. Although the piston 60, the guide shaft 52 and the plunger 80 are shown as separate components, it is contemplated these components can be integrally formed or connected to form a single piece.

The guide shaft 52, the piston 60 and the plunger 80 are moveable between the retracted position and the extended position, wherein movement from the retracted position to the extended or actuated position presents the IOL 20 to the patient. Each of the guide shaft 52, the piston 60 and the plunger 80 are moveable along a corresponding section of the lumen 39, and depending on the construction of the guide shaft, the piston and the plunger can be collinear or parallel.

As seen in FIGS. 1-4, and 11-13, the IOL injector 10 can include a first stop 180 and a second stop 190. The first stop 180 and the second stop 190 selectively block movement of the guide shaft assembly 50 along the longitudinal axis from the retracted position toward the extended position. Each of the first stop 180 and the second stop 190 are moveable between a blocking position, blocking further movement of the guide shaft assembly 50 and a passing position, permitting further movement of the guide shaft assembly. The first stop 180 and the second stop 190 can be used to control movement of the guide shaft assembly 50 along the longitudinal axis from the retracted position to a ready position, an actuated position and a venting position.

In one configuration, the first and the second stops 180, 190 are moveable from the blocking position to the passing position by sliding transverse to the longitudinal axis. However, it is understood the first stop 180 and the second stop 190 can be any of a variety of configurations. Referring to the Figures, the first stop 180 and the second stop 190 include a blocking portion 182, 192 and passing recess 184, 194, respectively each of which can be selectively aligned with a portion of the guide shaft assembly 50 to correspondingly block or permit movement of the assembly in the longitudinal direction.

In one configuration, the first stop 180 limits movement of the guide shaft assembly 50 along the longitudinal axis at a point where the IOL 20 has been folded as it moves at least partly from the shuttle 130, however the IOL remains within the IOL injector 54. Thus, a surgical technician can prep the IOL injector 10 for a surgeon by moving the guide shaft assembly 50 along the longitudinal axis from the retracted position to contact the first stop 180, thereby at least partly forming the IOL 20 into an injection configuration while reducing the risk of spontaneous (unintended) ejection of the IOL from the IOL injector. The IOL injector 10 is then provided to the surgeon who can move the first stop to the passing position and can control the mechanical brake 110 to move the guide shaft assembly from the position of the first stop to deliver the IOL 20 to the patient. It is understood the first stop 180 and the guide shaft assembly 50 can be configured such that upon contact with the first stop, the guide shaft assembly (and hence plunger 80) are at any of a variety of IOL 20 preparation positions, such as but not limited to prior to contact with the IOL, contacting the IOL, partially folding the IOL or fully disposing the IOL in an injection configuration.

Actuation of the first stop 180 (moving to the first stop to the passing position) followed by manipulation of the mechanical brake 110, allows continued movement of the guide shaft assembly 50 from the position of the first stop along the longitudinal axis until the guide shaft assembly contacts the second stop 190.

The second stop 190 can be located to limit movement of the guide shaft assembly 50 along the longitudinal axis at a point where the IOL 20 has been passed from the IOL injector 10 and a portion of the plunger tip 84 has passed from the IOL injector 10. Thus, the IOL injector 10 has fulfilled the function of presenting the IOL 20 to the patient and providing the plunger tip 84 for manipulation of the IOL during the insertion process.

As seen in FIGS. 2-4 and 13, the first stop 180 is initially disposed in the blocking position and can include a bias member acting to urge the first stop 180 to the blocking position or resist movement of the first stop 180 from the blocking position. The bias member can be any of a variety of constructions, such as projecting tab that is biased to urge the first stop 180 to the blocking position.

Figure 1:
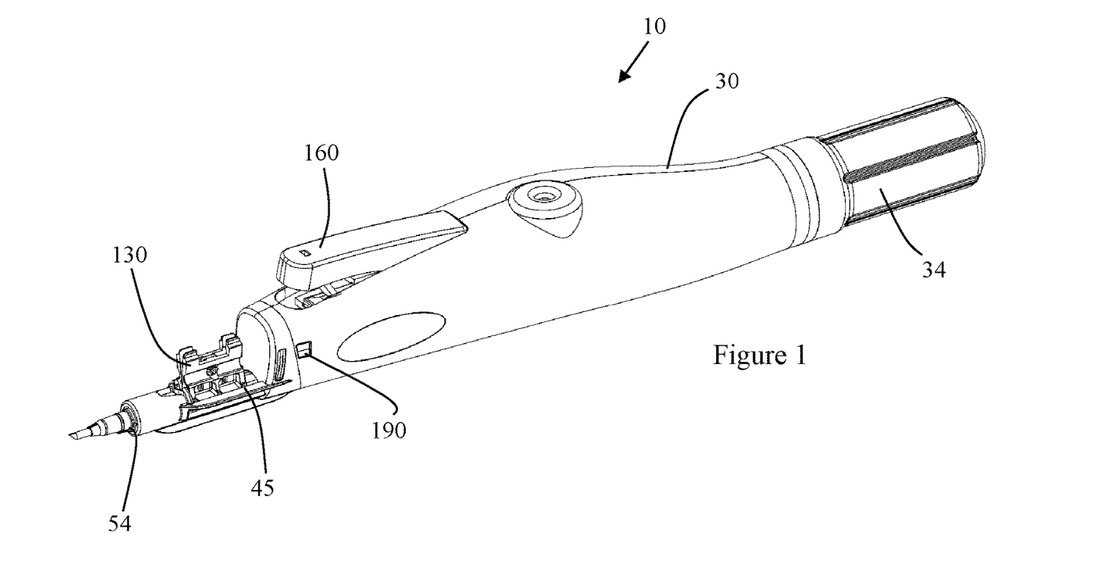
FIG. 1 is a left side perspective view of a first configuration of the IOL injector.
Figure 2:
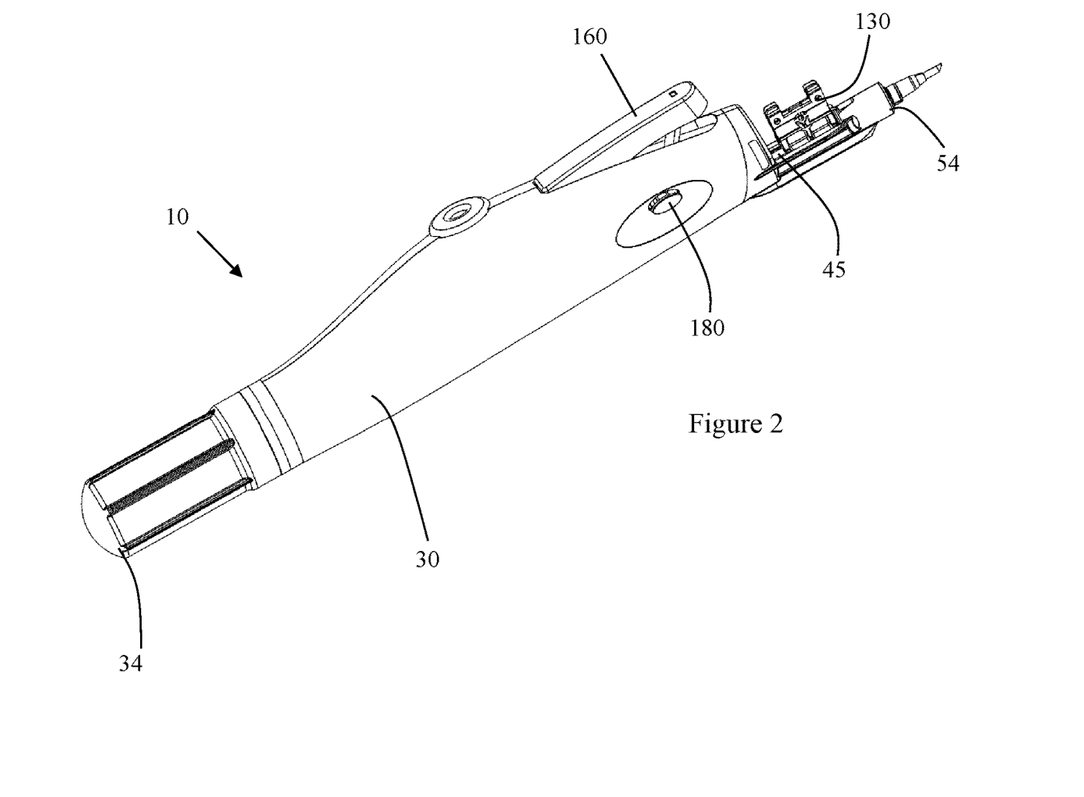
FIG. 2 is a right side perspective view of the IOL injector of FIG. 1.
Figure 3:
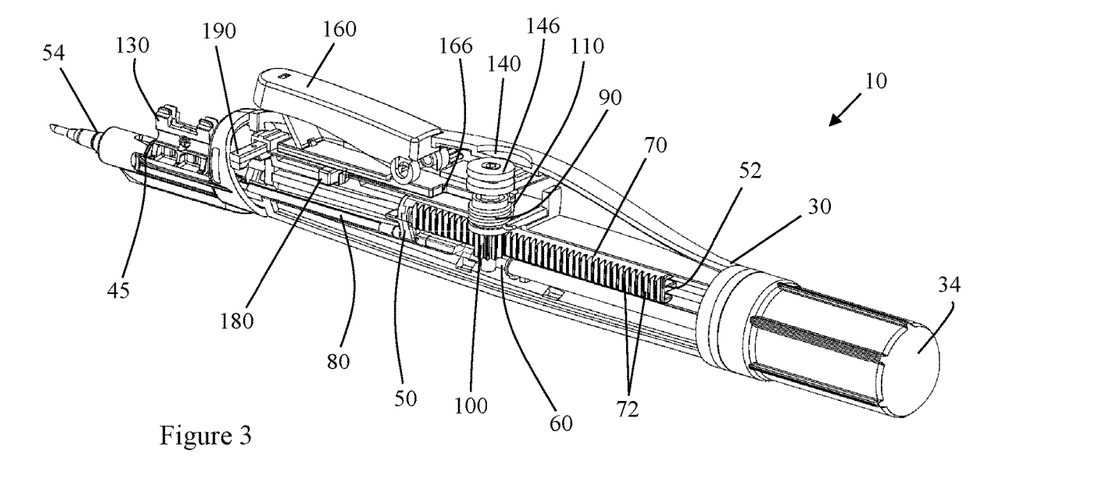
FIG. 3 is a left side perspective view of the IOL injector of FIG. 1, with a left side housing removed.
Figure 4:
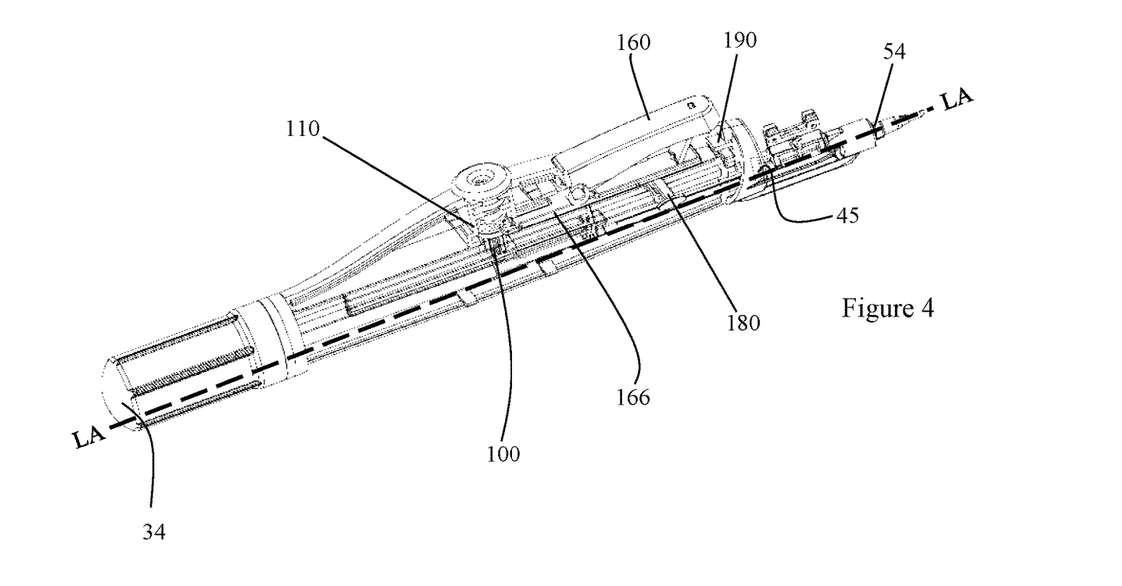
FIG. 4 is a right side perspective view of the IOL injector of FIG. 1, with a right side housing removed.
Figure 5:
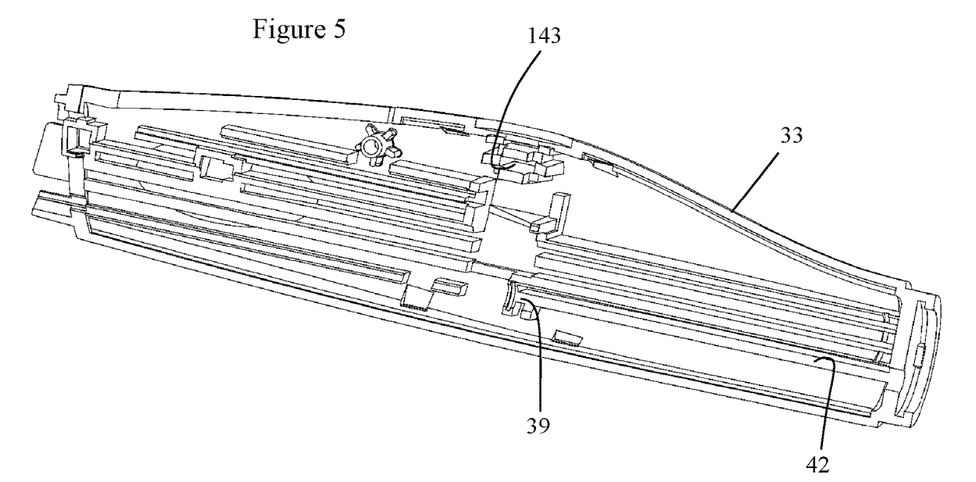
FIG. 5 is a perspective view of a right side housing of the IOL injector.
Figure 6:
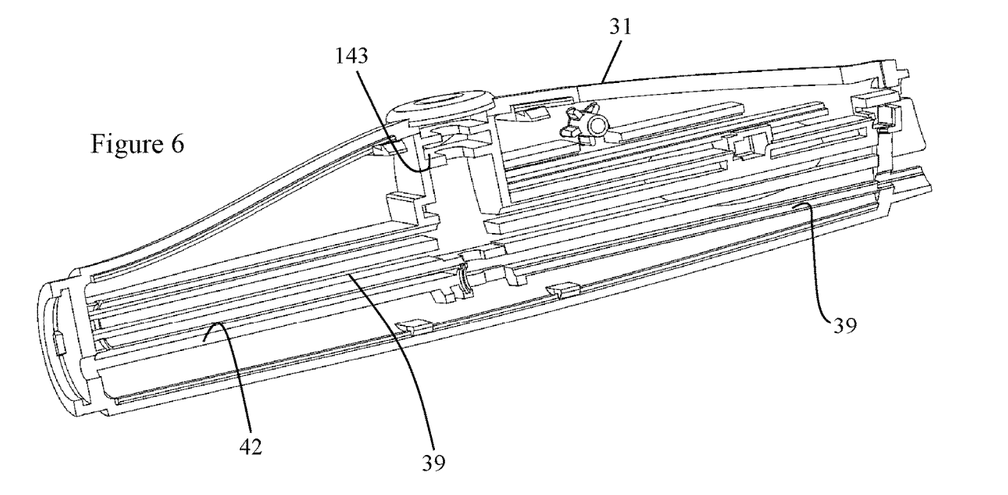
FIG. 6 is a perspective view of a left side housing of the IOL injector.
Figure 13:
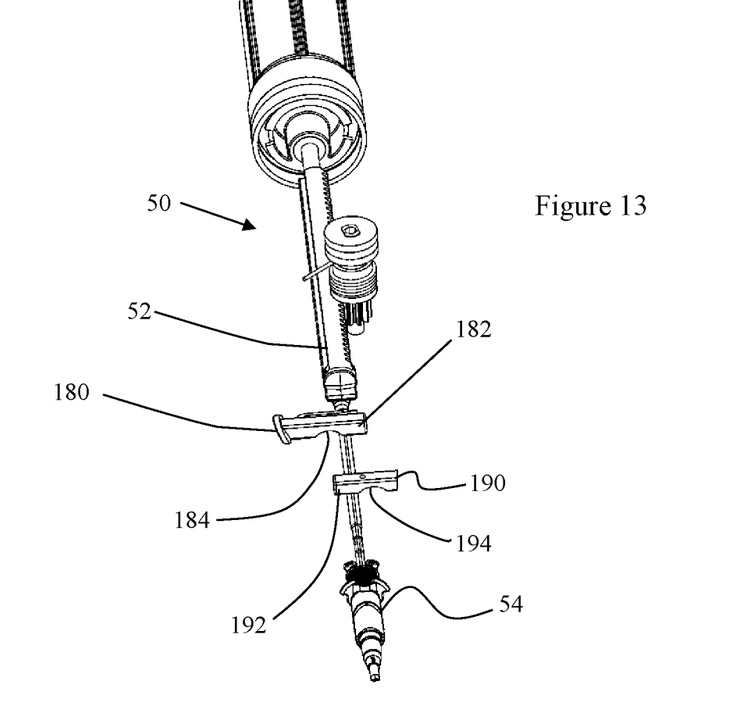
FIG. 13 is elevational, perspective view of a portion of the guide shaft assembly and a first stop and a second stop.

As seen in FIGS. 1, 3 and 13, the second stop 190 is also initially disposed in the blocking position. In one configuration, the second stop 190 is configured to at least substantially preclude actuation by use of just the hands of the operator. It is contemplated that a separate tool can be used to move the second stop 190 to the passing position, thereby allowing the venting of any remaining compressed gas.

That is, the compressed gas cartridge 124 is typically sized to retain an excess of compressed gas to ensure sufficient motive force for presenting the IOL 20. Thus, upon the guide shaft assembly 50 contacting the second stop 190, in this state, the compressed gas cartridge 124 typically retains a volume of compressed gas.

To reduce disposal concerns of the compressed gas cartridge 124 still retaining a mass of compressed gas, the second stop 190 can be moved to allow movement of the guide shaft assembly 50 past the second stop 190. This continued movement of the guide shaft assembly 50 allows the seal 62 to pass a vent port in the injector body 10 thereby allowing any higher than ambient pressure compressed gas to vent.

Movement of the guide shaft assembly 50 along the longitudinal axis from the retracted position towards the extended position causes the plunger tip 84 to contact the IOL 20, wherein the IOL is folded as it moves at least partly from the shuttle 130, however the IOL remains within the IOL injector.

Generally, the compressed gas imparts a force on the guide shaft assembly 50 (via the piston 60) to translate the guide shaft 52 along the longitudinal direction thereby moving the plunger 80 (and upon contact, the IOL 20) toward to the patient. The mechanical brake 110 initially precludes movement of the guide shaft 52 until operator input changes the mechanical resistance to the longitudinal translation.

The mechanical brake 110 selectively resists translation of the guide shaft 52, the plunger 80 and the piston 60 along the longitudinal axis. The mechanical brake 110 can have a variety of configurations which allow the operator to selectively vary the resistance to the longitudinal translation and hence speed of the passage of the IOL 20 through and from the injector 10.

In one configuration, the mechanical brake 110 includes a rack 70 with a plurality of teeth 72 on the guide shaft 52, wherein the teeth engage a rotatable gear 100, such as a pinion gear, and wherein rotation of the gear is mechanically retarded until variably changed by the operator. Although the guide shaft 52 and the rack 70 are shown as integral, it is understood the elements could be formed separately and subsequently joined to be a single piece construction.

In this one configuration, the mechanical brake 110 can include a variable friction member 90 acting on the gear 100 via a brake drum 112. The gear 100 and the brake drum 112 are coupled together and thus rotate together about a common axis relative to the injector body 30.

In this configuration, the mechanical brake 110 operates by limiting rotation of the gear 100 that is engaged with the guide shaft 52 (by means of the rack 70). The mechanical brake 110 can include the variable friction member, such as the wound brake coil 90 disposed about a portion of the brake drum 112, wherein the brake coil has a default configuration gripping the brake drum. That is, absent any operator input, the brake coil 90 engages or grips the brake drum 112 to preclude rotation of the gear 100 in response to exposure of the piston 60 to the compressed gas in the compressed gas chamber 32. As the brake coil 90 grips the brake drum 112 and is connected to the injector body 30, the brake drum is precluded from rotating. The brake coil 90 and the brake drum 112 are configured to preclude rotation of the brake drum (and hence rotation of the gear 100 and longitudinal translation of the guide shaft assembly 50) upon exposure of the piston 60 to the compressed gas in the compressed gas reservoir 32.

Referring to FIGS. 3, 4, 9, 11 and 12, the variable mechanical resistance can be accomplished by adjustment of the brake coil 90 about the brake drum 112. The adjustment is provided by a release lever 160 acting on brake slide 166, which is turn is connected to the brake coil 90. The release lever 160 is rotatable about a rotation axis through a range of motion between a maximum braking position and a minimum braking position. The release lever 160 is coupled to the brake slide 166 by a link 164 pivotally connected at each end between the release lever and the brake slide 166. By virtue of the rotation of the release lever 160 and the pivoting connection of the link 164 between the lever and the brake slide 166, the amount of travel of the brake slide (and hence amount of change in the force applied by the brake) decreases for a given amount of rotation of the release lever as the release lever operates near the minimum braking position. That is, not only does the rotation of the release lever 160 allow continuous adjustment of the braking force (and hence continuous adjustment of the movement of the guide shaft assembly 50), but the change in braking force for a given movement of the release lever decreases as the release lever operates near the minimum braking force range.

The brake slide 166 extends between the release lever 160 and the brake coil 90. The brake slide 166 includes a catch 169 for engaging a portion of the brake coil 90. In one configuration, an end of the brake coil 90 projects from the brake drum 112 and engages the catch 169, wherein the brake coil exerts a bias against the catch and hence the brake slide 166. This bias on the brake slide 166 urges the brake slide to pivot the link 164 to rotate the release lever 160 to the maximum braking force position, or the stop position. Operator imparted rotation of the release lever 160 about the pivot 163 causes the link 164 to move the brake slide 166 along the longitudinal axis in the longitudinal direction. As the brake slide 166 is connected to the brake coil 90, the longitudinal translation of the brake slide 166 tends to loosen the brake coil relative to the brake drum 112, thereby allowing rotation of the brake drum and hence the gear 100. While the rotation of the release lever 160 and relaxing of the brake coil 90 are shown as infinitely adjustable (not stepped), it is contemplated that movement of either or both could be stepped or incremented, such as by teeth or steps on one of the surfaces.

As the gear 100 engages the teeth 72 of the rack 70 (and the rack is coupled to or part of the guide shaft 52), permitting rotation of the brake drum 112 and gear 100 allows corresponding longitudinal translation of the guide shaft. The mechanical brake 110 is also connected to the injector body 30 and movable between (i) an engaged maximum braking position, precluding rotation of the gear 100 and thus precluding longitudinal movement of the rack 70 and hence the guide shaft 52 (and the plunger 80) relative to the injector body and (ii) a retracted position permitting rotation of the gear and thus corresponding longitudinal movement of the rack, the guide shaft and the plunger relative to the injector body. By varying the friction of the brake coil 90 on the brake drum 112, the mechanical brake 110 can apply a variable resistance to rotation of the gear 100 and hence longitudinal movement of the guide shaft assembly 50. Thus, the velocity of longitudinal translation of the guide shaft 52 can be operator controlled by the mechanical brake 110.

Partial unwinding (or loosening) of the brake coil 90 on the brake drum 112 reduces the resistance to rotation of the gear 100 and hence reduces the resistance to longitudinal translation of the guide shaft assembly 50. Thus, loosening the brake coil 90 about the brake drum 112, the operator can selectively vary the engagement of the mechanical brake 110 to control the translational movement of the guide shaft assembly 50 (and hence plunger 80) along the longitudinal direction.

In one configuration, a control knob 116 can be selectively engaged with the brake drum 112 to impart rotation of the gear 100 to move the guide shaft assembly 50 in the longitudinal direction to retract the plunger 80. The control knob 116 is rotatable to be able to move the rack 70 (via rotation of the gear 100), and hence the guide shaft 52 and the plunger 80, toward the first retracted position, away from the patient. Thus, the operator can reverse the direction of movement of the guide shaft 52 and the plunger 80, as necessary.

Although the mechanical brake 110 is shown as the brake coil 90 and the brake drum 112 with the gear 100 coupled to the brake drum, it is understood the mechanical brake can be any of a variety of mechanical engagements that selectively permit and preclude movement of the guide shaft assembly 50 along the longitudinal direction in response to the exposure of the piston 60 to the compressed gas.

Thus, the mechanical brake 110 can include, for example, a pressure pad or wheel that is biased to engage the guide shaft assembly 50, wherein operator input acts against (or changes) the bias of the mechanical brake to reduce engagement with the guide shaft 52, such that the force on the piston 60 from the compressed gas overcomes the resistance to motion and the plunger 80 is allowed to move in a controlled translation. Alternatively, the mechanical brake 110 can include, for example, an endless belt that engages the guide shaft assembly 50 and a roller or idler, wherein motion of the belt is selectively restricted, such as by restricting rotation of the roller or compression upon the belt.

As seen in FIGS. 3, 9, 10 and 11, the injector 10 can include a limiter 140 for limiting the velocity or establishing a maximum velocity of the guide shaft assembly 50 along the longitudinal axis. In one configuration, the injector body 30 includes at least one, and as seen in the figures, a plurality of cavities 143, wherein each cavity is sized to receive a corresponding plate or disk 146. The plates 146 are disposed about a portion of the brake drum 112 and are couple to the brake drum so as to rotate with the brake drum and hence the gear 100. A thick grease or paste, used as a viscous dampener, can be disposed in the cavity 143, wherein the grease is selected to impart sufficient friction on the plates 146 to limit rotational velocity of the plates, and hence the gear 100 and thus the guide shaft assembly 50. Thus, even if the mechanical brake 110 is released to its fullest extent, a maximum velocity of the plunger 80 is set by the limiter 140. The IOL injector 10 provides for single hand operation as the injector body is sized to fit into a hand. Further, as the mechanical brake 110 is selectively variable, the operator, by using the hand that is retaining the IOL injector 10 can manipulate the release lever 160 to control presentation of the IOL 20 to the patient, to provide single hand operation.

Operation

In select configurations, the IOL injector 10 is shipped and stored in a storage position, wherein the compressed gas cartridge is sealed and has not been punctured. Thus, the guide shaft assembly 50 is not exposed to the compressed gas.

The shuttle 130 carrying the retained IOL 20 is engaged with the injector body 30. To dispense the IOL 20 from the injector body 30, the compressed gas reservoir 32 is filled with compressed gas 120, such as by selectively piercing the compressed gas cartridge 124. The piston 60 is thus exposed to the compressed gas 120 which exerts a force on the piston, urging the piston toward the extended position.

The mechanical brake 110 defaults to an engaged configuration as the brake coil 90 and precludes rotation of the brake drum 112 and hence precludes rotation of the gear 100. As the gear 100 is engaged with the guide shaft assembly 50 via the rack 70 (and the guide shaft 52 is connected to the piston 60) there is no movement of the guide shaft assembly. Thus, there is initially no movement of the guide shaft assembly 50 and hence no movement of the plunger 80 upon the piston 60 being exposed to the compressed gas.

Once the operator desires to initiate the procedure to introduce the IOL 20 to the patient, the mechanical brake 110 is at least partially released (by depressing the release lever 160 and relaxing the brake coil 90 about the brake drum 112), allowing rotation of the gear 100, which allows the rack 70 and the guide shaft 52 to translate longitudinally in response to exposure of the compressed gas 120 with the piston 60. Specifically, the release lever 160 is rotated thereby sliding the brake slide 166 to loosen the brake coil and allow the brake drum to begin to rotate, thereby allowing the piston 60 to move in response to the compressed gas in the compressed gas reservoir 32.

As the piston 60 moves, the guide shaft 52, the rack 70 and the plunger 80 also move relative to the injector body 30 in the longitudinal direction along the longitudinal axis. The movement of the rack 70 and hence guide shaft assembly 50 corresponds to rotation of the gear 100. This movement causes the plunger 80 to contact the IOL 20 and transition the IOL from the shuttle 130 (or storage position) into the injector tip 54.

At this point, the guide shaft assembly 50 contacts the blocking portion 182 of the first stop 180 and further translation of the plunger 80 is stopped.

While it has been described as the compressed gas moving the guide shaft assembly 50 to contact the first stop 180, it is contemplated that the operator can manually move the guide shaft assembly 50 from the retracted or storage position to contact the first stop 180. With the guide shaft assembly 50 engaged with the first stop 180, and further movement along the longitudinal axis precluded, the compressed gas cartridge 124 can then opened/punctured so that the compressed gas acts on the piston 60. In this, position of the guide shaft assembly 50 both the mechanical brake 110 and the first stop 180 prohibit further translation of the guide shaft assembly (and hence plunger 80) relative to the injector body.

The first stop 180 can then be disposed to the passing position aligning the passing recess 184 with the guide shaft assembly 50, and the mechanical brake 110 continues to preclude movement of the guide shaft assembly 50 (and hence plunger 80) relative to the injector body 30. The release lever 160 is then controlled by the operator to selectively permit movement of the guide shaft assembly 50 including the plunger 80 and the IOL 20.

Upon the operator releasing or reducing pressure on the release lever 160, the brake coil 90 increases engagement with the brake drum 112, thereby inhibiting rotation of the brake drum. The inhibited rotation of the brake drum 112 inhibits longitudinal movement of the guide shaft 52 and the plunger 80. By varying the amount of engagement of the brake coil 90 and the brake drum 112 (by varying the movement of the release lever 160), the operator can vary the speed of plunger 80 translating along the longitudinal direction.

Since the mechanical brake 110 defaults to a status or position that precludes longitudinal translation of the plunger 80, only upon operator input of at least partly releasing the mechanical brake 110, is the guide shaft 52 allowed to translate along the longitudinal direction.

Thus, the termination of operator input at any point causes the mechanical brake 110 (via the brake coil 90 to stop rotation of the brake drum 112) to halt movement of the rack 70 and hence the IOL 20 towards the patient.

As set forth above, the guide shaft assembly 50 can then move toward the extended position until the guide shaft assembly contacts the blocking portion 192 of the second stop 190. In this position, a portion of the plunger tip 84 projects from the injector tip 54, thereby allowing the operator to use the injector tip as necessary to orient or locate the IOL 20 relative to the patient.

If the operator desires to reverse the plunger 80, the control knob 116 can be engaged with the brake drum 112 and actuated to retract the rack 70, and hence plunger 80.

Upon completion of the procedure, the second stop 190 can be moved to the passing position aligning the passing recess 194 with the guide shaft assembly 50 thereby allowing the compressed gas to further move the piston 60 and expose the vent port to the compressed gas reservoir 32, thereby venting any remaining compressed gas from the compressed gas cartridge 124 and the IOL injector 10.

Having thus described the inventive concepts and a number of exemplary embodiments, it will be apparent to those skilled in the art that the invention may be implemented in various ways, and that modifications and improvements will readily occur to such persons. Thus, the embodiments are not intended to be limiting and presented by way of example only. The invention is limited only as required by the following claims and equivalents thereto.

The invention claimed is:

1. An intraocular lens (IOL) injector comprising:
   (a) a compressed gas reservoir for retaining a compressed gas;
   (b) a guide shaft assembly exposed to the compressed gas reservoir, the guide shaft assembly being moveable along a longitudinal direction from a retracted position to an extended position;
   (c) a mechanical brake operably coupled to the guide shaft assembly, the mechanical brake configured to exert on the guide shaft assembly, in response to an operator actuation, a variable resistance to the longitudinal movement of the guide shaft assembly, the mechanical brake having a default engagement with the guide shaft assembly to preclude movement of the guide shaft assembly in response to exposure of the guide shaft assembly to compressed gas in the compressed gas reservoir;
   (d) a limiter connected to the guide shaft assembly, the limiter configured to limit a velocity of the guide shaft assembly in response to exposure of the guide shaft assembly to the compressed gas, wherein the limiter includes a disk and a viscous dampener, the disk configured to rotate through the viscous dampener, and the viscous dampener selected to impart friction on the disk; and
   (e) a first stop moveable between (i) a passing position permitting movement of the guide shaft assembly from the retracted position to the extended position and (ii) a blocking position precluding movement of the guide shaft assembly to the extended position.

2. The IOL injector of claim 1, wherein the guide shaft assembly includes a piston, the piston located to be exposed to the compressed gas reservoir.

3. The IOL injector of claim 1, wherein the guide shaft assembly includes a plunger tip.

4. The IOL injector of claim 1, wherein the mechanical brake includes a rotatable brake drum and a gear connected to the brake drum.

5. The IOL injector of claim 4, wherein the mechanical brake includes a resilient brake coil wrapped about the rotatable brake drum.

6. The IOL injector of claim 1, wherein the compressed gas reservoir retains a constant mass of the compressed gas.

7. The IOL injector of claim 1, wherein a mass of the compressed gas is sufficient to fully translate the guide shaft assembly from the retracted position to the extended position.

8. The IOL injector of claim 1, wherein the mechanical brake returns to the default engagement with the guide shaft assembly upon cessation of operator actuation.

9. The IOL injector of claim 1, wherein the guide shaft assembly moves along the longitudinal direction from the retracted position to the extended position in response to the compressed gas in the compressed gas reservoir.

10. An intraocular lens (IOL) injector comprising:
    (a) a compressed gas reservoir for retaining a compressed gas;
    (b) a guide shaft assembly exposed to the compressed gas reservoir, the guide shaft assembly being moveable along a longitudinal direction from a retracted position to an extended position, the guide shaft assembly including a guide shaft, a plunger and a piston, the plunger including an elongate plunger shaft and a plunger tip, the plunger tip being configured to engage an IOL; and
    (c) a mechanical brake operably coupled to the guide shaft, the mechanical brake configured to exert on the guide shaft assembly, in response to an operator actuation, a variable resistance to the longitudinal movement of the guide shaft assembly, the mechanical brake having a default engagement with the guide shaft assembly to preclude movement of the guide shaft assembly in response to exposure of the guide shaft assembly to compressed gas in the compressed gas reservoir,
    wherein the guide shaft and at least a portion of one of the plunger shaft and the piston are non-coaxial and occupy a common length along the longitudinal direction,
    wherein a majority of a length of the guide shaft and a majority of a length of the piston occupy a common length along the longitudinal direction.

11. The IOL injector of claim 10, wherein the guide shaft engages the mechanical brake.

12. The IOL injector of claim 10, wherein the plunger shaft and the plunger tip are coaxial.

* * * * *